United States Patent
Ochi et al.

(10) Patent No.: US 7,061,242 B2
(45) Date of Patent: Jun. 13, 2006

(54) MAGNETIC RESONANCE IMAGING SYSTEM

(75) Inventors: Hisaaki Ochi, Kokubunji (JP); Yo Taniguchi, Kokubunji (JP); Tetsuhiko Takahashi, Souka (JP); Ken'ichi Okajima, Mitaka (JP)

(73) Assignee: Hitachi Medical Corporation, Tokyo (JP)

( * ) Notice: Subject to any disclaimer, the term of this patent is extended or adjusted under 35 U.S.C. 154(b) by 294 days.

(21) Appl. No.: 10/432,166

(22) PCT Filed: Nov. 20, 2001

(86) PCT No.: PCT/JP01/10131

§ 371 (c)(1),
(2), (4) Date: Sep. 29, 2003

(87) PCT Pub. No.: WO02/39896

PCT Pub. Date: May 23, 2002

(65) Prior Publication Data

US 2004/0061498 A1 Apr. 1, 2004

(30) Foreign Application Priority Data

Nov. 20, 2000 (JP) .................................. 2000-353118

(51) Int. Cl.
*G01V 3/00* (2006.01)

(52) U.S. Cl. ........................ 324/318; 324/322
(58) Field of Classification Search ................ 324/318, 324/322, 309, 307, 314, 311; 600/422; 128/653
See application file for complete search history.

(56) References Cited

U.S. PATENT DOCUMENTS

| 5,280,246 A | * | 1/1994 | Takahashi et al. | 324/322 |
| 5,389,880 A | * | 2/1995 | Mori | 324/318 |
| 5,951,474 A | * | 9/1999 | Matsunaga et al. | 600/422 |
| 6,172,503 B1 | * | 1/2001 | Mori | 324/318 |
| 6,556,012 B1 | * | 4/2003 | Yamashita | 324/318 |

FOREIGN PATENT DOCUMENTS

| JP | 6-47020 A | * | 2/1994 |
| JP | 9-131332 | * | 7/1995 |

OTHER PUBLICATIONS

Ra et al; Fast Imaging, Magnetic Resonance in Medicine vol. 8; pp142–145, 1993.*

* cited by examiner

*Primary Examiner*—Btij B. Shrivastav
(74) *Attorney, Agent, or Firm*—Antonelli, Terry, Stout & Kraus, LLP

(57) ABSTRACT

To provide a diagnostic apparatus utilizing nuclear magnetic resonance suitable for interventional MRI which is not limited as to selection of an imaging section and an phase-encoding axis, the reception coil thereof includes three loop coils arranged so as to surround an object to be examined and to be within a plane including a line segment parallel to a static magnetic field direction, and two surface coils arranged in the vicinity of the surface of the object within a plane including a line segment perpendicular to the static magnetic field direction. In the reception coil, two or more sub-coils have nonuniform sensitivity profiles along an arbitrary axis. Therefore, the reception coil configured to have sensitivity throughout the imaging areas can be realized.

32 Claims, 17 Drawing Sheets

(a)

(b)

(c)

(d)

MAGNETIC RESONANCE IMAGING SYSTEM

FIELD OF THE INVENTION

The present invention relates to a magnetic resonance imaging (MRI) apparatus; and, more particularly, the invention relates to an MRI apparatus that is suitable for interventional MRI.

BACKGROUND OF THE INVENTION

An MRI apparatus is characterized in that high tissue-contrast resolution can be obtained, and desired tomograms can be obtained; and, such an apparatus has no invasiveness, for example. The application of an MRI apparatus, having such characteristics, not only to diagnostic imaging, but also to interventional MRI, such as is used in connection with the guiding of a biopsy needle, the monitoring of therapy, the guiding of an endoscope and a catheter, and the like, has been drawing increased attention. In interventional MRI, a device, such as a biopsy needle and a catheter, is inserted in the body of the object to be examined, while an operator (a doctor) observes the position of the device using MR images. That is, the device in the object, the position of which changes with time, is continuously imaged, and a plurality of thus obtained images are sequentially displayed on a display, whereby the doctor can guide the device to a lesion during surgery.

On the other hand, with regard to an MRI apparatus, a technology for shortening the imaging time utilizing plural coils and performing aliasing in images is being put into practical use (conventional technique 1: J. B. Ra, C. Y. Rim: Fast Imaging Using Subencoding Data Sets from Multiple Detectors, MAGNETIC RESONANCE in Medicine, vol.30, pp.142–145 (1993)).

The conventional technique 1 involves a method of shortening the imaging time to 1/(sub-coil number) by using a reception coil having a plurality of sub-coils. For example, when two sub-coils are used, the desired field of view (FOV) is divided into halves along the phase-encoding direction, and the halves are respectively imaged by two coils at the same time, whereby the imaging time is cut in half. The two half FOV images include aliasing artifacts of the object. However, the artifacts are removed by solving simultaneous equations utilizing the different sensitivity distributions of the two coils, whereby a 1/1 FOV image is reconstructed.

FIGS. 10(a) and 10(b) are diagrams illustrating the conventional technique. A method of removing aliasing artifacts will be described with reference thereto. FIG. 10(a) shows a representative example of measurement data in phase space, or k-space (left side of FIG. 10(a)), and a real-space image (right side of FIG. 10(a)) when a desired FOV (one FOV image) is imaged using a conventional method with one coil. The measurement data of the k-space is subject to Fourier Transformation (F.T.) so as to be converted into a real-space image.

FIG. 10(b) shows a representative example of measurement data in k-space (left side of FIG. 10(b)) and a real-space image (right side of FIG. 10(b)), when imaging is performed using a method of shortening the imaging time by utilizing an array-coil having two sub-coils and aliasing artifacts of images. Both in FIG. 10(a) and FIG. 10(b), the x-direction indicates the readout direction, and the y-direction indicates the phase-encoding direction.

In the k-space measurement data in FIG. 10(b), the width of the interval between steps in the phase-encoding direction is twice as broad as that of the k-space measurement data in FIG. 10(a). When the k-space measurement data in FIG. 10(b) is subject to Fourier transformation, the FOV is narrowed in the y-direction to produce the real-space image in FIG. 10(b), and a portion of the object that does not fit in the FOV appears as aliasing artifacts. In the real-space image in FIG. 10(b), pixels at S, which is an overlap of aliasing artifacts, represent an overlap of the pixels located on A and B in the real space image in FIG. 10(a).

Here, in the image obtained by Fourier-transforming signals measured by the first of the two sub-coils, the signal intensity (luminance) of the pixel located at S is represented by $V_{S1}$, and in the image obtained by Fourier-transforming signals measured by the second of the two sub-coils, the signal intensity of the pixel located at S is represented by $V_{S2}$. The sensitivity of the first sub-coil to the pixel located at A with a standard value is represented by $f_{1A}$, and its sensitivity to the pixel located at B with a standard value is represented by $f_{1B}$. Similarly, the sensitivity of the second sub-coil to the pixel located at A with a standard value is represented by $f_{2A}$, and its sensitivity to the pixel at B with a standard value is represented by $f_{2B}$. Magnetization existing on the pixels located at A is represented by $I_A$, and magnetization existing on the pixels located at B is represented by $I_B$. At this time, the relation of formula (1) is valid.

$$\begin{vmatrix} V_{S1} \\ V_{S2} \end{vmatrix} = \begin{vmatrix} f_{1A} & f_{1B} \\ f_{2A} & f_{2B} \end{vmatrix} \begin{vmatrix} I_A \\ I_B \end{vmatrix} \quad (1)$$

A pre-scanning is performed so as to calculate the sensitivity distribution of plural sub-coils constituting the reception coil, and the elements of the matrix $f_{1A}$, $f_{1B}$, $f_{2A}$, and $f_{2B}$ in the formula (1) are calculated in advance. Since $V_{S1}$ and $V_{S2}$ can be calculated, unknowns $I_A$ and $I_B$ are calculated by solving the matrix equation of formula (1).

The number of rows in the matrix corresponds to the number of sub-coils. For example, when the sub-coil number is eight, the number or rows in the matrix is eight. At the same time, the number of columns in the matrix has to be no more than the sub-coil number. For example, when the sub-coil number is eight, the number of columns in the matrix has to be eight or less. This is because the number of unknowns in the simultaneous equations must be no more than the number of equations.

FIG. 11 shows an example of the arrangement of a reception coil (array-coil) 118 as used in the conventional technique. The reception coil 118 includes a plurality of rectangular coils arranged on the surface of the object to be examined 103. The output of the reception coil 118 is sampled at a receiver 108 and is stored in the memory of a computer 109.

Usually, when two coils are placed close to each other, the resonance point of the input impedance of the coils is divided into two or more, due to mutual inductive coupling. Among the plurality of sub-coils constituting the reception coil 118, the adjacent sub-coils are usually overlapped moderately, as shown in FIG. 11, so as to eliminate the mutual inductive coupling. If the degree of overlapping is not appropriate, the resonance point of the input impedance of the coils is divided into two or more. By serially connecting a subsidiary coil to each of the adjacent coils, the inductive coupling between the adjacent coils can be eliminated without overlapping.

In a conventional imaging method, an image is generated only from positional information in the phase-encoding direction obtained by a gradient magnetic field. On the other hand, in the imaging method according to the conventional technique 1, the sensitivity distribution of the reception coil is actively utilized, along with the gradient magnetic field, in generating an image from the positional information in the phase-encoding direction. The imaging-time shortening technique, according to the conventional technique 1, is effective in speeding up all imaging methods from the usual imaging method to an ultra-fast imaging method.

To use the speed-up technique according to the conventional technique 1, one or more sub-coils having nonuniform sensitivity distributions in the phase-encoding direction of an MR image of an imaging section are required. By "nonuniform sensitivity distribution", it is meant that, in the area of the object being examined, there is a point where the sensitivity of the coil is half the highest sensitivity.

FIGS. 8(a), 8(b), 8(c), and 8(d) show a loop coil 91-2 according to the present invention, the sensitivity distribution 81 thereof along the x-axis, the sensitivity distribution 82 thereof along the y-axis, and the sensitivity distribution 83 thereof along the z-axis, respectively. As shown in FIG. 8(a), the diameter of the loop coil 91-2 is 40 cm, and the loop coils 91-1 and 91-3 (not shown) have the same diameter. Among the sensitivity distributions along the respective axes, only the sensitivity distribution 82 on the y-axis has, within the area of the object, some points where the sensitivity is half or less than the highest sensitivity.

Generally, when the number of sub-coils having a nonuniform sensitivity profile in the phase-encoding direction, among the plurality of sub-coils constituting the reception coil, is n, the speed with which a desired FOV (1/1 FOV image) is imaged can be raised (n+1)-fold compared to that when one coil only is used, by using the conventional technique 1. In the following description, the improved ratio of imaging speed is referred to as an imaging speed-up ratio. However, when the imaging-speed raising ratio is represented by N, the sensitivity distributions of N or more sub-coils need to be different from each other.

In the formula (1), if the relation shown in the formula (2) is valid, the matrix in the formula (1) does not have an inverse matrix and the solution thereof is indefinite.

$$f_{1A}:f_{1B}=f_{2A}:f_{2B} \quad (2)$$

FIGS. 12(a) to 12(d) show examples of an imaging section and sensitivity distributions along certain lines. FIG. 13 shows an example of the arrangement of the loop coils according to the present invention. In FIG. 13, the z-axis corresponds to a static magnetic field direction. The loop coil 91-1, which is disposed on a plane intersecting with the xz plane at an angle of 45°, and the loop coil 91-3, which is disposed on a plane intersecting with the xz plane at an angle of −45°, are arranged on the outer periphery of the object 103. The imaging section 121 is set to the xy plane, and the FOV is set from −15 cm to 15 cm. As shown in FIG. 12(a), the imaging section is determined by the x-axis and the y-axis.

Here, the phase-encoding direction is set to the y-direction. FIG. 12(b) shows the sensitivity distributions 123-1 and 123-2 of the coils 91-1 and 91-2, respectively, on a line segment 122-1 parallel to the y-axis. FIG. 12(c) shows the sensitivity distributions 124-1 and 124-2 of the coils 91-1 and 91-2, respectively, on a line 122-2 parallel to the y-axis. FIG. 12(d) shows sensitivity distributions 125-1 and 125-2 of the coil 91-1 and 91-2, respectively, on a line 122-3 parallel to the y-axis.

As shown in FIG. 12(c), the sensitivity distributions 124-1 and 124-2 match each other. The sensitivity distributions 123-1 to 125-2 shown in FIGS. 12(b), 12(c), and 12(d) are nonuniform sensitivity distributions along the y-axis. When using the speed-up technique, the aliasing artifact on the line segments 122-1 and 122-3 can be removed by using the difference between the sensitivity distributions of the two coils. However, the aliasing artifact on the line segment 122-2 cannot be removed, since the sensitivity distributions of the two coils on the line segment 122-2 are the same.

Also, when the values of $f_{1A}/f_{1B}$ and $f_{2A}/f_{2B}$ are not completely the same, but are close to each other, that is, when the sensitivity distributions of the two sub-coils are similar, a problem occurs in that, when image reconstruction is performed, the S/N ratio of the image is deteriorated on the lines along which the sensitivity distributions of the two sub-coils are similar.

The speed-up according to the conventional technique 1 has been hitherto developed mainly for an apparatus of the horizontal magnetic field type with high magnetic field, and various structures of reception coils for use in the horizontal-magnetic-field-type apparatus have been proposed. On the other hand, an open MRI apparatus of the vertical magnetic field type using a superconductive magnet or a permanent magnet, has been drawing attention in recent years.

FIG. 3 is a perspective view of an open-type MRI apparatus according to the present invention. Since the open MRI apparatus of the vertical magnetic field type has a large opening, as shown in FIG. 3, a doctor 114 can directly access the object 103, whereby this apparatus is suitable for interventional MRI.

Since the direction of an RF (Radio Frequency) magnetic field generated by coils needs to be perpendicular to the direction of a static magnetic field, the structure of the reception coil also needs to be changed when the direction of the static magnetic field is changed from horizontal to perpendicular. The arrangement of the reception coil for the apparatus of a vertical magnetic field type also has been proposed (conventional technique 2: G. Randy Duensing, et. al.: A 4-channel Volume Coil for Vertical Field MRI, ISMRM, p1398 (2000)). However, in the structure proposed hitherto, there is a problem in that the imaging speed-up ratio can only be improved by twice when the phase-encoding direction is set to the static magnetic field direction.

The speed-up technique described in the conventional technique 1 is effective for imaging moving organs, such as the heart. To deal with fast movement of an organ, like the heart, the imaging speed-up ratio needs to be improved by three times or more.

However, among the four sub-coils mentioned in the conventional technique 2, only one sub-coil has a nonuniform sensitivity profile in the static magnetic field direction. Therefore, if such sub-coils are applied to the speed-up technique, the imaging speed-up ratio can be improved by three times or more by setting the phase-encoding direction to a direction different from the static magnetic field direction. However, when the phase-encoding direction is set to the static magnetic field direction, the imaging speed-up ratio can be improved by only twice.

That is, when imaging a transverse plane which is often used in the imaging of the heart, there is a problem in that the imaging speed cannot be sufficiently raised when the phase-encoding direction is set to a direction of chest-to-back (static magnetic field direction). The imaging speed can be raised by setting the phase-encoding direction to a direction other than the static magnetic field. However, in the imaging of the heart, there is a problem that the user's need for freely setting the phase-encoding direction in order to reduce artifacts of blood flow is not satisfied.

Also, an array-coil has been proposed which has figure-eight coils 117 as the sub-coils, as shown in FIG. 2 (conventional technique 3: Japanese Patent Laid-open Publication JP-A-04-282132). FIG. 4 shows RF current directions (arrows in the figure) on the figure-eight coils 117 according to the conventional technique. FIG. 5 shows RF magnetic fields generated by the figure-eight coils 117 shown in FIG. 4, wherein the arrows represent the direction of the RF magnetic fields and the size of the arrows represents the size of the RF magnetic fields. FIG. 6 shows the sensitivity of the figure-eight coils 117 shown in FIG. 4, wherein the size of the arrows represents the size of the sensitivity.

Among the RF magnetic fields shown in FIG. 5, only the component perpendicular to the static magnetic field contributes to the NMR phenomenon. Therefore, the distribution of sensitivity is generated as indicated by the arrows in FIG. 6. That is, the figure-eight coils 117 shown in FIG. 4 have a sensitivity above and below conductors 41 and 42, and the sensitivity profile thereof has a gradient in the y-direction. When a plurality of the figure-eight coils 117 arranged as shown in FIG. 2, an array-coil, including two or more sub-coils having nonuniform sensitivity profile on an arbitrary axis, can be formed.

However, since the figure-eight coils 117 have a sensitivity only above and below the conductors 41 and 42 in FIG. 4, there is a problem that the sensitivity of all sub-coils, except in the portion below the conductors 41 and 42, is significantly deteriorated when performing imaging on a coronal plane (xy plane) with the arrangement of the coils shown in FIG. 2. Consequently, there is an area in the FOV in which the coils do not have a sensitivity.

Therefore, the object of the present invention is to provide an MRI apparatus that is suitable for interventional MRI, in which selection of the imaging section and the phase-encoding axis is not limited.

SUMMARY OF THE INVENTION

In the MRI apparatus according to the present invention, the reception coil includes a plurality of loop-coils arranged on the periphery of an object within a plane including a line segment that is substantially parallel to a static magnetic field direction and a plurality of surface coils arranged in the vicinity of the surface of the object on a plane including a line segment that is substantially perpendicular to the static magnetic field direction. The sub-coils (loop coils and surface coils) constituting the reception coil are arranged so as not to electrically interfere with each other. The number of the loop coils constituting the reception coil is three or more, and the number of the surface coils is two or more. By employing such a structure, the reception coil can be formed such that two or more sub-coils having a nonuniform sensitivity profile exist on an arbitrary axis, and there is no portion of the imaging area in which the coils hardly have a sensitivity; that is, the coils have a sensitivity in the entire imaging area.

The MRI apparatus according to the present invention includes means for generating a static magnetic field in the vertical direction, means for generating an exciting RF pulse to be applied to an object to be examined, which is placed in the static magnetic field, means for generating gradient magnetic fields, and a reception coil, including a plurality of sub-coils, for detecting nuclear magnetic resonance signals that are generated from the object. The reception coil includes, for example, five or more sub-coils.

The sub-coils include two or more surface coils that are arranged in the vicinity of the surface of the object within a plane substantially perpendicular to the vertical direction and three or more loop coils arranged on the periphery of the object within a plane including an axis substantially parallel to the vertical direction. Two or more sub-coils have nonuniform sensitivity distributions along one of the two axes perpendicular to each other, which determine the chosen quadrate or rectangular imaging section in the object.

At least one sub-coil has a sensitivity at an arbitrary position in an arbitrary imaging section. At least two nonuniform sensitivities of two or more sub-coils arranged along a line parallel to one of two axes perpendicular to each other are different from each other on a line parallel to one of the two axes that are perpendicular to each other.

The respective surface coils are arranged in the vicinity of the object, inside or outside the three or more loop coils. The surface coils are figure-eight coils. The loop coil has a rectangular shape or a rectangle bend in the vicinity of ends of opposing sides.

The two or more surface coils include a first figure-eight surface coil and a second figure-eight surface coil, overlapping the first figure-eight surface coil. The output terminals of the first surface coil and that of the second surface coil are arranged respectively in directions perpendicular to each other.

When imaging is performed, the length of the rectangular FOV is set as 1/N (N is an integer, no less than two) of the length of the imaging section in the phase-encoding direction. Aliasing artifacts are removed from the image of the object being imaged so as to include the aliasing artifacts in the encoding direction, and the image of the imaging section is reconstructed. The pixel number of the reconstructed image is set as 128×128. When the rectangular coordinate system is set as (x, y, z) and the vertical direction is set to the z-direction, the phase-encoding direction is arbitrarily chosen to be the x-, y-, or z-direction.

Further, the MRI apparatus according to the present invention, being definable in a rectangular coordinate system (x, y, z) in which the z axis is in the vertical direction and the y axis is in the longitudinal direction, includes means for generating a static magnetic field in the z-direction, means for generating gradient magnetic fields in the x-, y-, and z-direction, and a coil including five or more sub-coils for detecting nuclear magnetic resonance signals generated from the object. An arbitrary imaging section is determined by two axes that are perpendicular to each other.

The sub-coil includes a first figure-eight surface coil arranged in the vicinity of the surface of the object within a fourth plane that is substantially parallel to the xy plane, a second figure-eight surface coil overlapping the first surface coil within the fourth plane, a first loop coil arranged on the periphery of the object within a first plane that is substantially parallel to the xz plane, a second loop coil arranged on the periphery of the object within a second plane intersecting with the first plane at about an angle of 45°, and a third loop coil arranged on the periphery of the object within a third plane intersecting with the first plane at about an angle of −45°.

The first and the second surface coils are arranged in the vicinity of the object, inside or outside the first, second and third loop coils.

The two or more sub-coils have a nonuniform sensitivity distribution along either of the two axes that are perpendicular to each other, which determine an arbitrary quadrate or rectangular imaging section In the object.

BEST MODE FOR CARRYING OUT THE INVENTION

Figure 1:
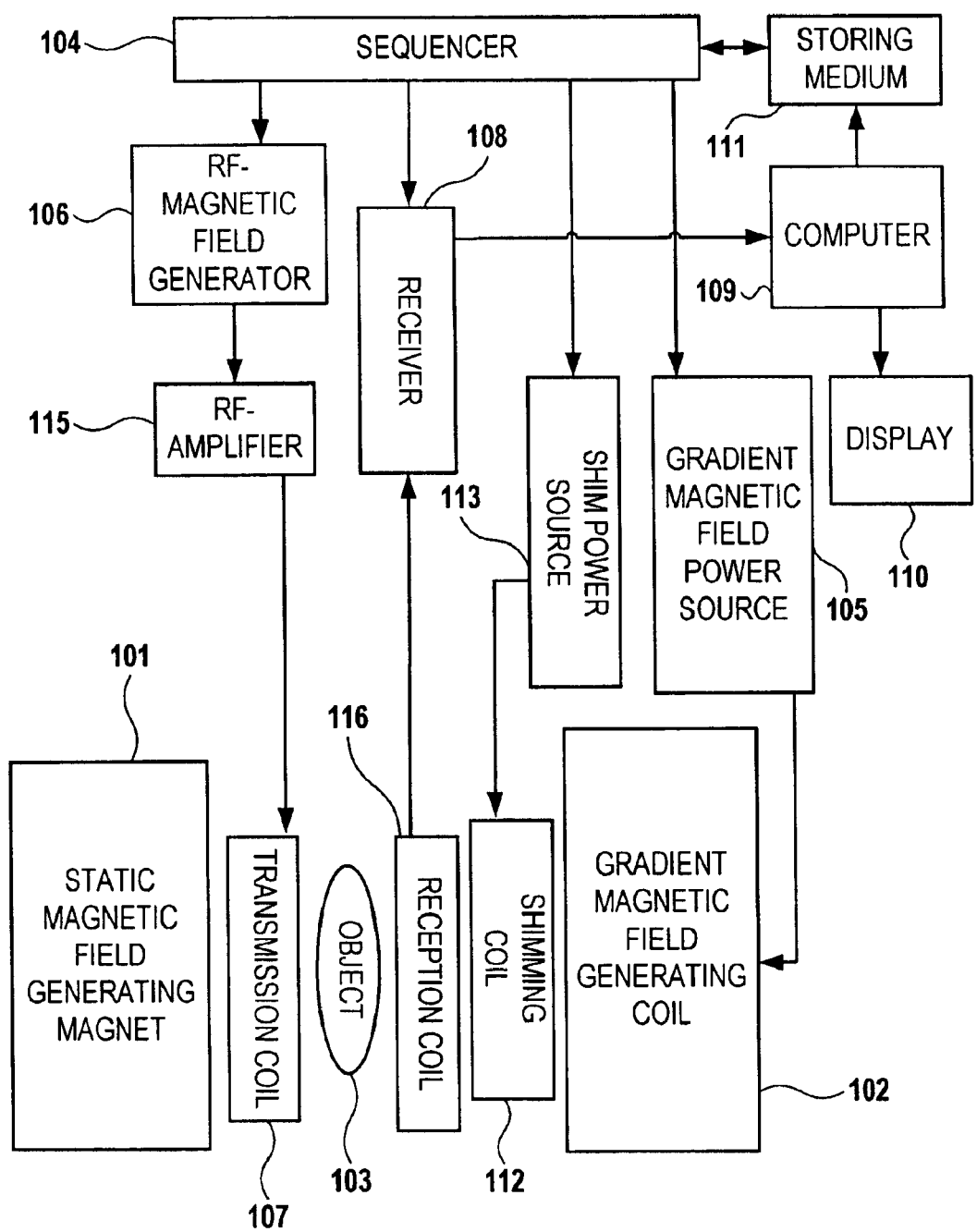
FIG. 1 is a block diagram showing an example of an apparatus according to the present invention.
Figure 2:
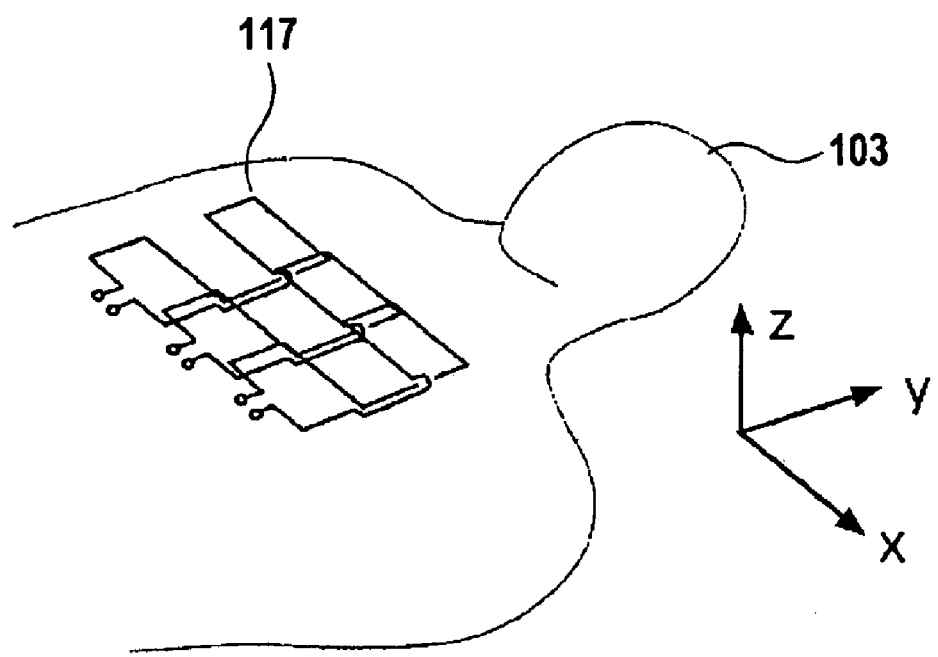
FIG. 2 is a diagrammatic view showing an example of the arrangement of a reception coil according the conventional technique.
Figure 3:
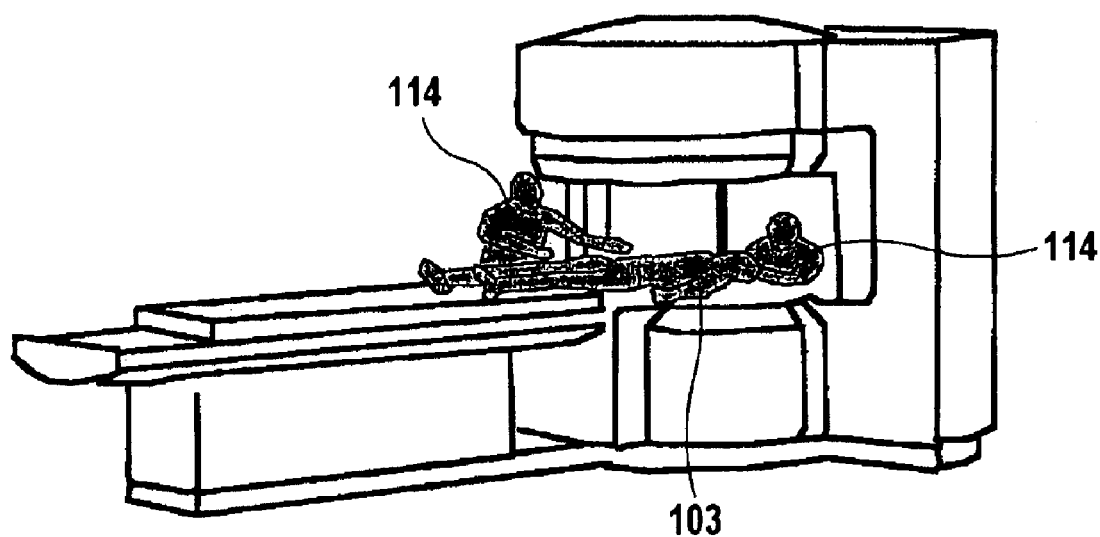
FIG. 3 is a perspective view showing an open-type MRI apparatus according to the present invention.
Figure 4:
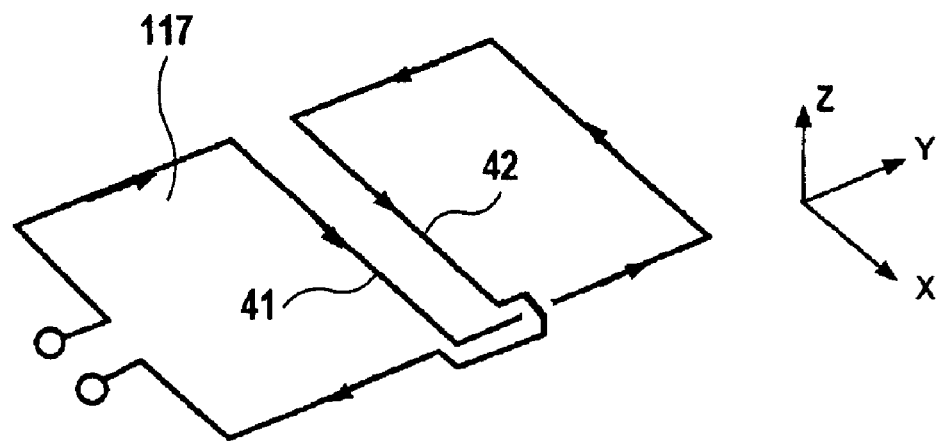
FIG. 4 is a diagram showing a direction of RF current in a figure-eight coil according to the conventional technique.
Figure 5:
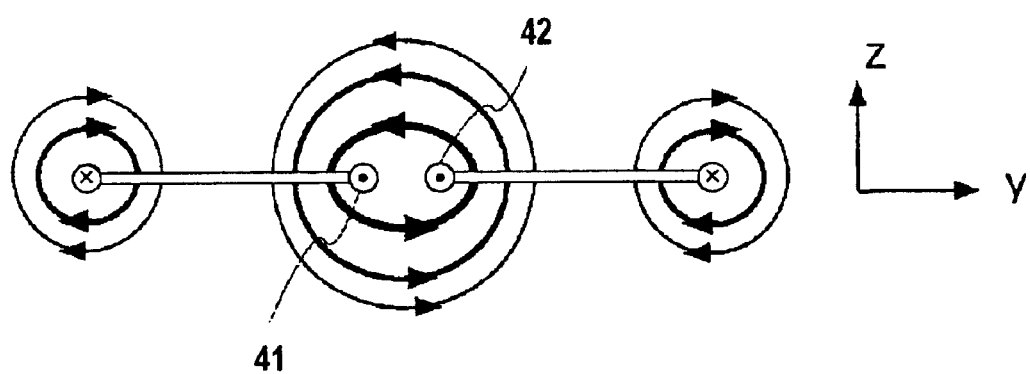
FIG. 5 is a diagrammatic view showing RF magnetic fields generated by the figure-eight coil shown in FIG. 4.
Figure 6:
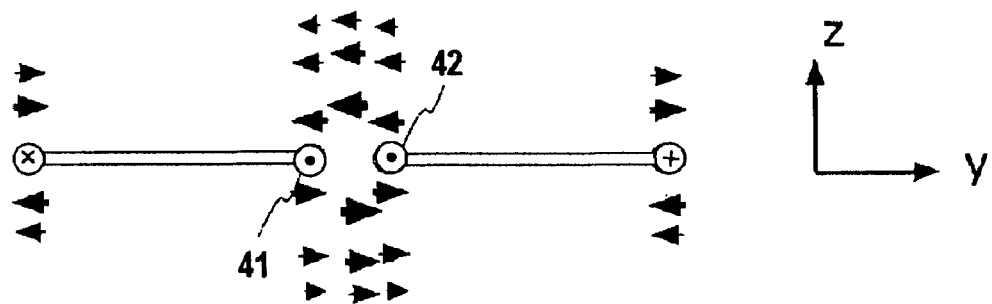
FIG. 6 is a diagram showing the sensitivity of the figure-eight coil shown in FIG. 4.

FIG. 1 is a block diagram showing an example of the structure of an MRI apparatus according to the present invention. As shown in FIG. 1, an object 103 is placed in a magnetic-field space, where a static magnetic field generated by a magnet 101 and gradient magnetic fields generated by a coil 102 are superposed. Generally, the gradient magnetic field generating coil 102 includes gradient magnetic field coils located on three axes intersecting with one another at right angles.

A sequencer 104 transmits an instruction to a gradient magnetic field power source 105 and a radio-frequency magnetic field (RF pulse) generator 106 such that gradient magnetic fields and an RF pulse are generated by the gradient magnetic field coil 102 and a transmission coil 107, respectively. Usually, the RF pulse output by the radio-frequency magnetic field generator 106 is amplified by an RF power amplifier 115, and it is applied to the object 103 from the transmission RF coil 107. Nuclear magnetic resonance (NMR) signals generated from the object 103 are received by a reception RF coil 116. The reception RF coil 116 may be inserted to the interior of the object 103.

The signals received by the reception RF coil 116 are subject to A/D conversion (sampling) at a receiver 108, and they are detected. A center frequency (magnetic resonance frequency), which is to be a standard of detection, is set by the sequencer 104. The detected signals are sent to a computer 109 and re-sampled, and they are then subject to signal processing such as image reconstruction. The result of the signal processing is displayed on the display 110. If necessary, the detected signals and the measuring conditions are stored in a storing medium 111.

If the uniformity of the static magnetic field needs to be adjusted, a shimming coil 112 is used. The shimming coil 112 has a plurality of channels, and current is transmitted from a shim power source 113 to the shimming coil 112. In the adjustment of the static magnetic field uniformity, the value of current transmitted to each coil of the plural channels is controlled by the sequencer 104. The sequencer 104 sends an instruction to the shim power source 113, and an additional magnetic field for correcting a nonuniformity of the static magnetic field is generated by the shimming coil 112.

Incidentally, the sequencer 104 controls the respective portions of the apparatus, such that they work at a programmed timing and with programmed intensity. Among the programs, a program for controlling the application of the RF pulse, the application of the gradient magnetic fields, the timing of reception of the nuclear magnetic resonance signal, and the intensity of the RF pulse and the gradient magnetic fields is particularly referred to as an imaging sequence, or a pulse sequence.

Figure 9:
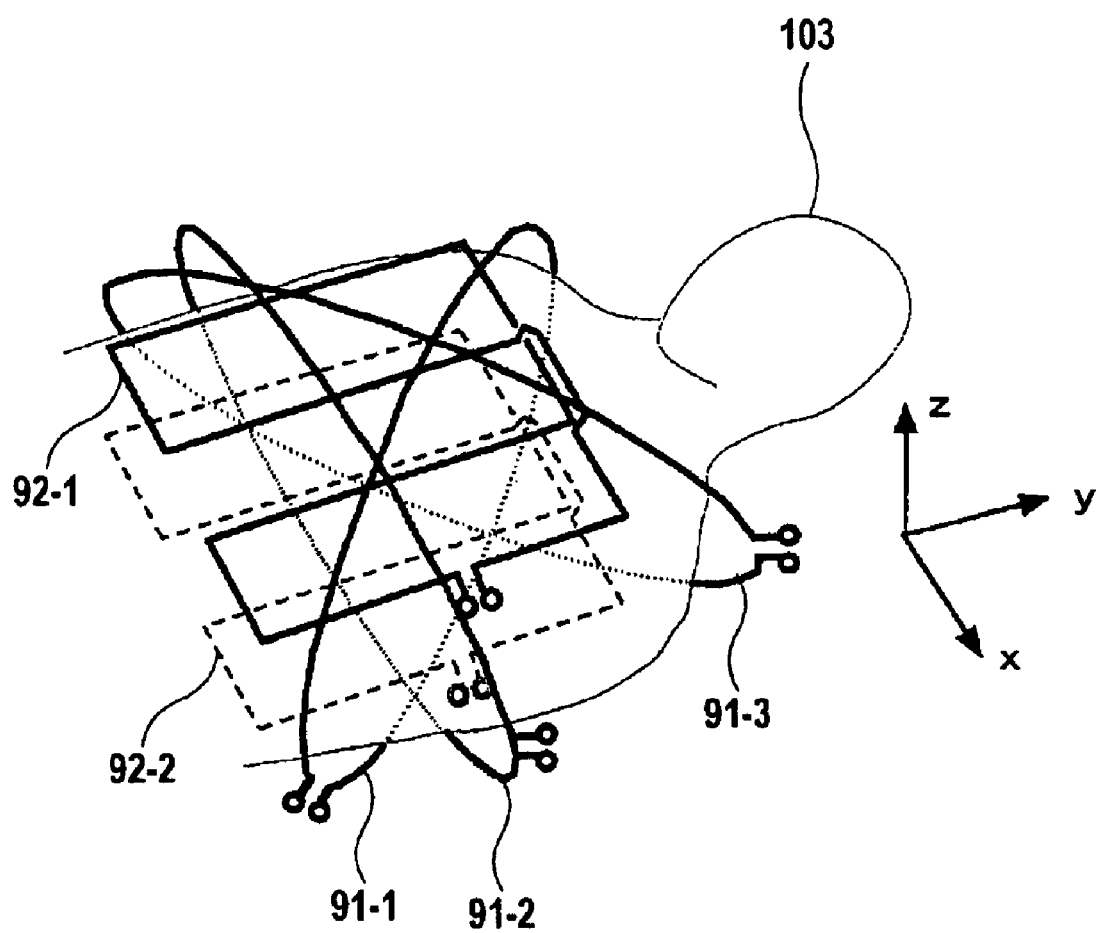
FIG. 9 is a diagrammatic view showing an example of the arrangement of a reception coil according to the present invention.
Figure 10:
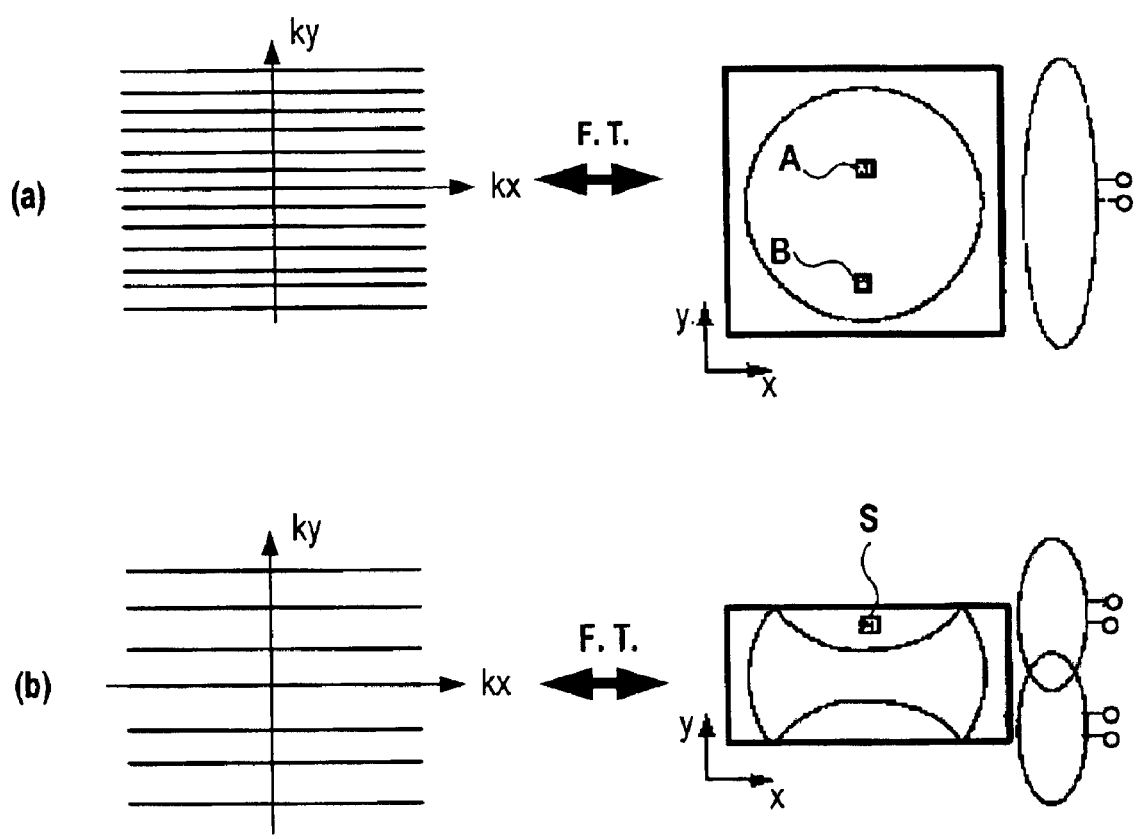
FIGS. 10(a) and 10(b) are diagrams illustrating the conventional technique.
Figure 11:
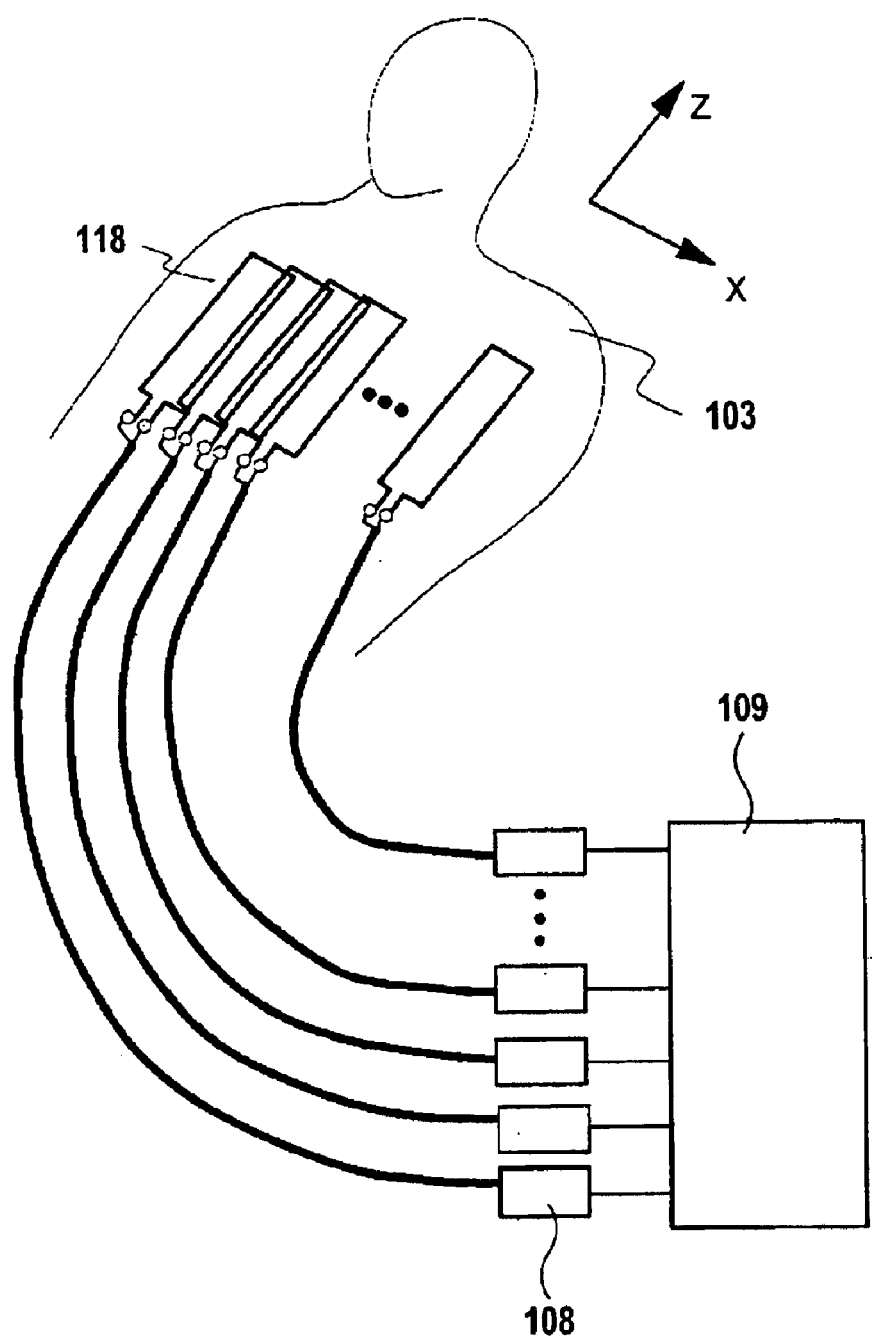
FIG. 11 is a diagrammatic view showing an example of the arrangement of a reception coil according to the conventional technique.
Figure 12:
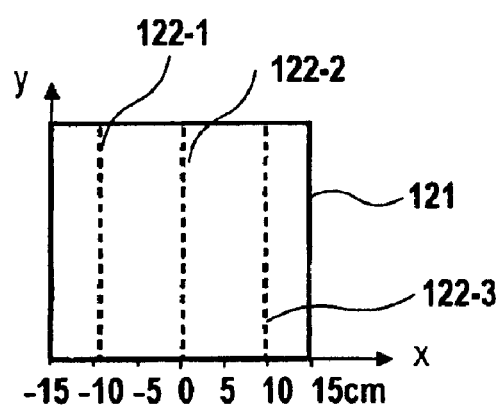
FIGS. 12(a), 12(b), 12(c) and 12(d) are graphs showing sensitivity distributions of loop coils according to the present invention.
Figure 12:
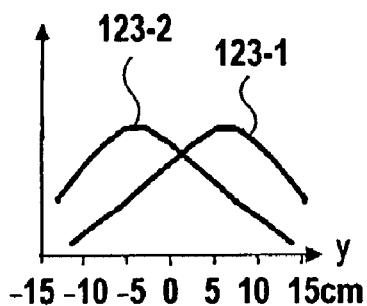
Figure 12:
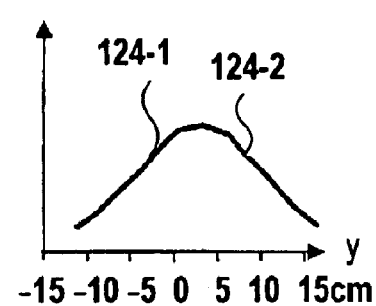
Figure 12:
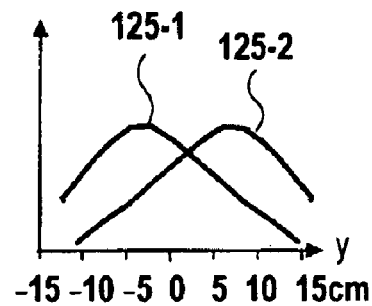
Figure 13:
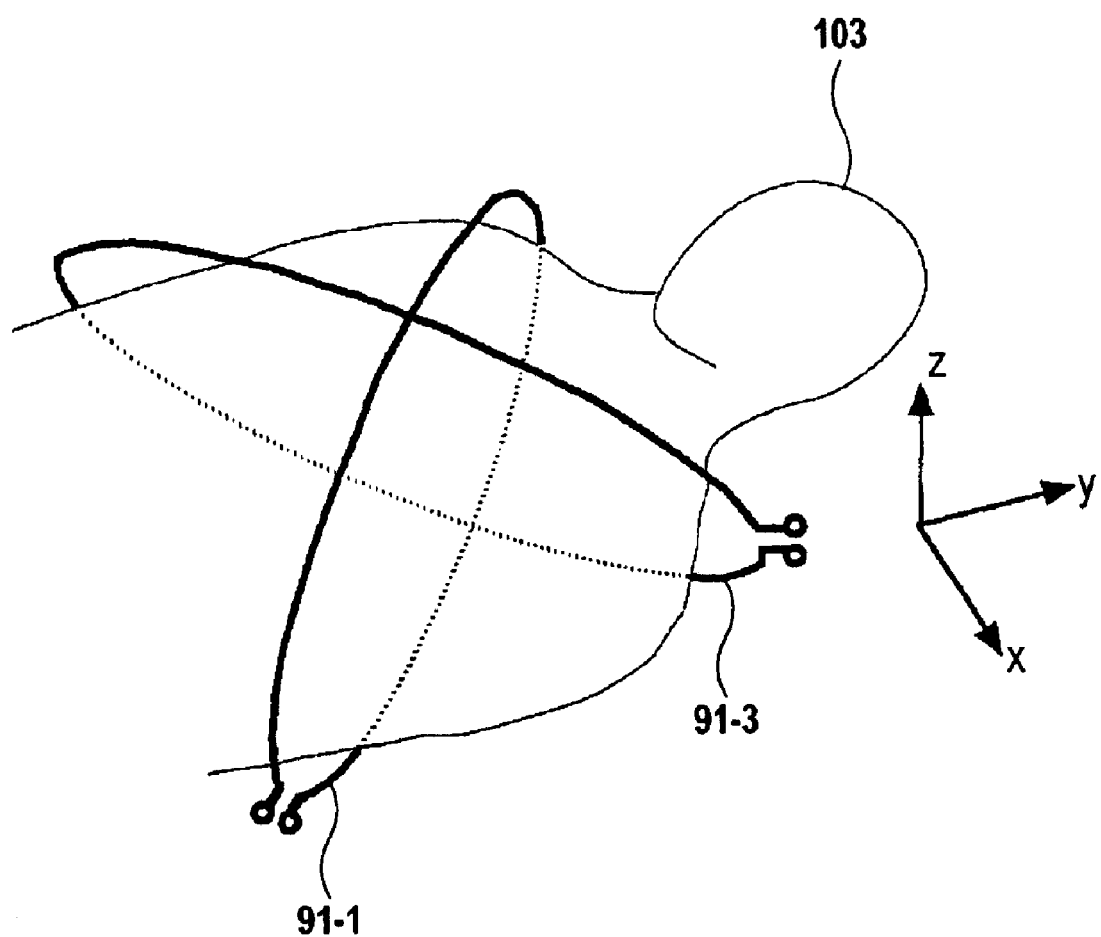
FIG. 13 is a diagrammatic view showing an example of the arrangement of loop coils according to the present invention.

According to the present invention, the reception coil 116 shown in FIG. 1 includes a plurality of sub-coils. FIG. 9 is a diagram showing an example of an arrangement of the reception coil according to the present invention. The following is a description of the case where the speed-up technique described in the conventional technique 1 is applied to the reception coils that are arranged as shown in FIG. 9.

The reception coil shown in FIG. 9 has five sub-coils, including three loop coils and two surface coils. The reception coil shown in FIG. 9 has loop coils 91-1, 91-2, and 91-3, which are arranged on the periphery of the object within a plane including a line segment that is substantially parallel to the static magnetic field direction (z-direction), and figure-eight coils 92-1 and 92-2, which are arranged in the vicinity of the surface of the object within a plane including a line segment that is substantially perpendicular to the static magnetic field direction.

The loop coil 91-2 is arranged within a first plane parallel to the xz plane. The loop coil 91-1 is arranged within a second plane intersecting with the first plane at a 45° angle. The loop coil 91-3 is arranged within a third plane intersecting with the first plane at a −45° angle. When actually arranging these coils, it is difficult to arrange the coils strictly at 45° or at −45°. However, it is preferable to arrange the coils at least in the ranges 45° to 50°, and −40° to −50°, respectively.

As for the surface coils, the figure-eight coil 92-1 is arranged in the vicinity of the surface of the object's chest, and the figure-eight coil 92-2 is arranged in the vicinity of the surface of the object's back. The centers of the two figure-eight coils are located on the z-axis passing through the origin of the imaging section.

Figure 7:
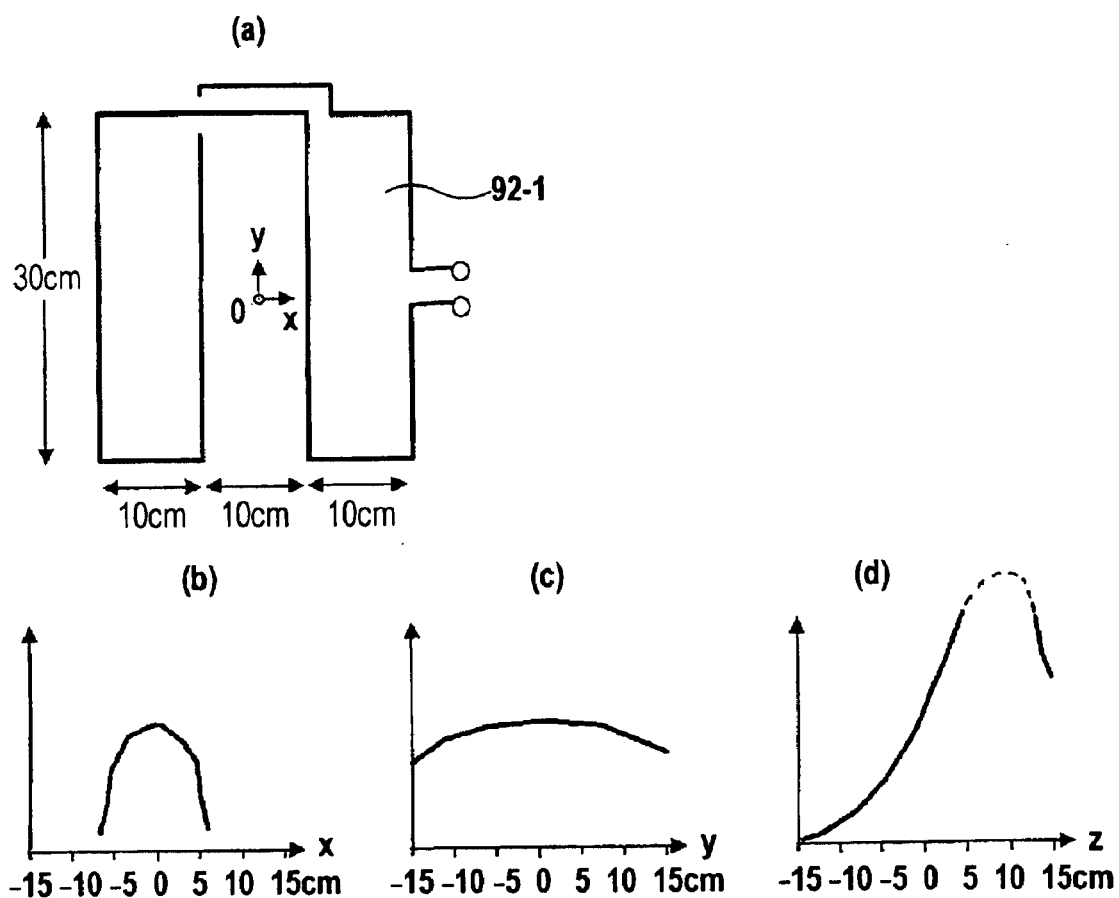
FIGS. 7(a), 7(b), 7(c), and 7(d) are diagrams showing sensitivity distributions of a figure-eight coil according to the present invention.
Figure 8:
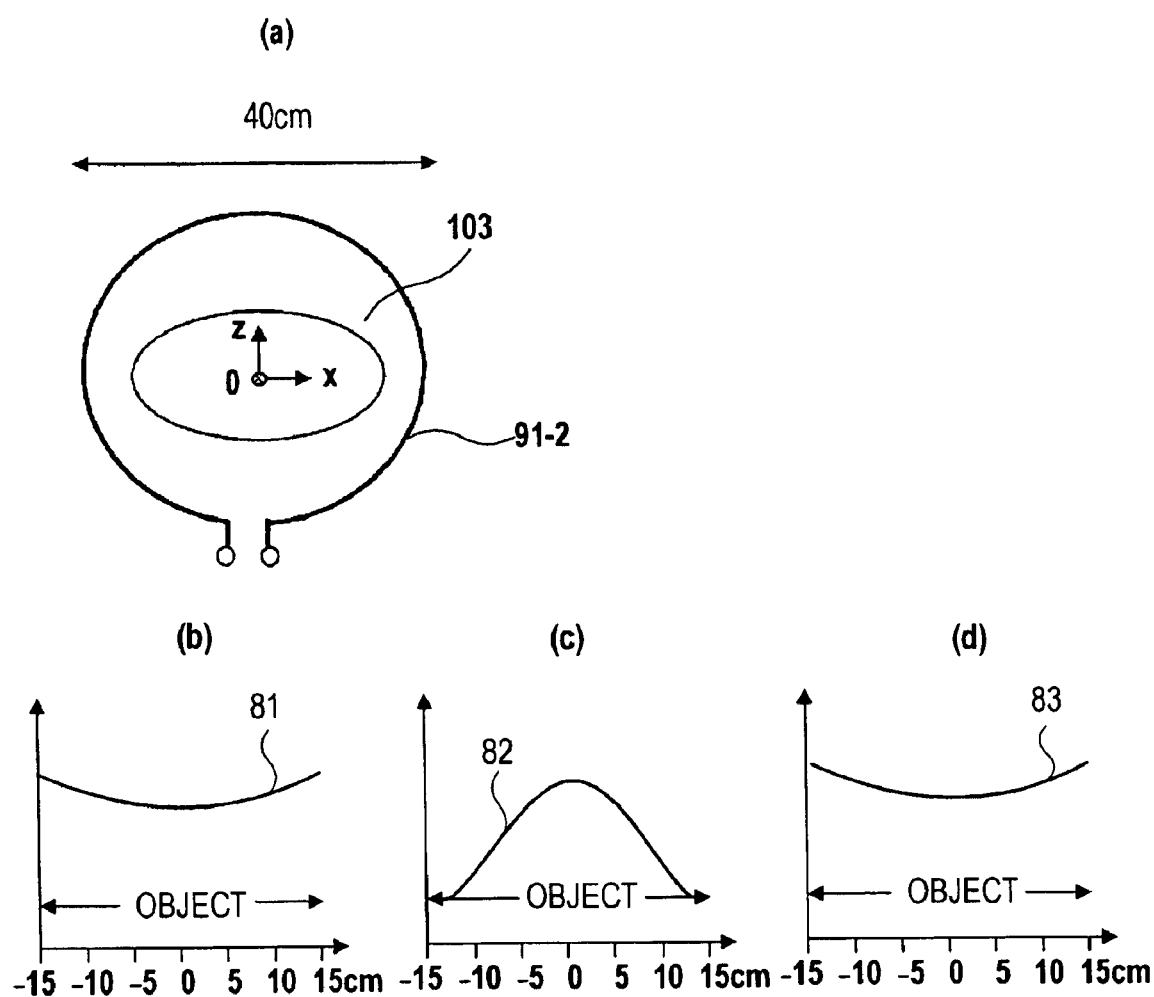
FIGS. 8(a), 8(b), 8(c), and 8(d) are diagrams showing sensitivity distributions of a loop coil according to the present invention.

FIG. 7 shows the sensitivity distributions of the figure-eight coil according to the present invention. FIGS. 7(*b*)–7(*d*) show the sensitivity distributions of the figure-eight coil 92-1, shown in FIG. 7(*a*), on the x-, y-, and z-axes, respectively, passing through the origin of the imaging section. As shown in FIG. 7(*a*), the figure-eight coil has two rectangular conductive loops that are spaced from each other by 10 cm, the width thereof being 10 cm and the length being 30 cm.

Figure 14:
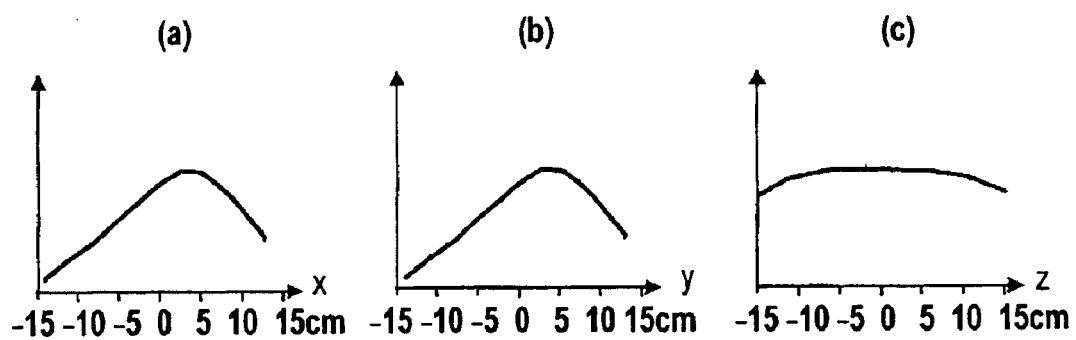
FIGS. 14(a), 14(b) and 14(c) are graphs showing sensitivity distributions of one of the loop coils according to the present invention.

FIG. 14(*a*), FIG. 14(*b*), and FIG. 14(*c*) show respective sensitivity distributions of the loop coil 91-1 along the x-, y-, and z-axes passing through the origin.

Figure 15:
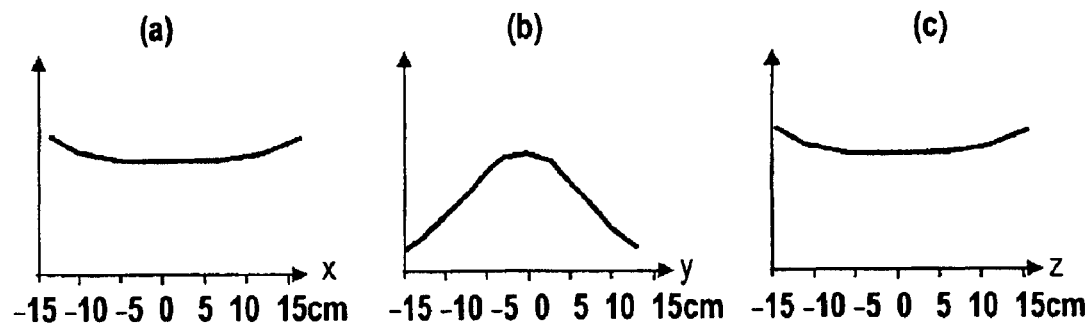
FIGS. 15(a), 15(b) and 15(c) are graphs showing sensitivity distributions of one of the loop coils according to the present invention.

FIG. 15(*a*), FIG. 15(*b*), and FIG. 15(*c*) show respective sensitivity distributions of the loop coil 91-2 along the x-, y-, and z-axes passing through the origin.

Figure 16:
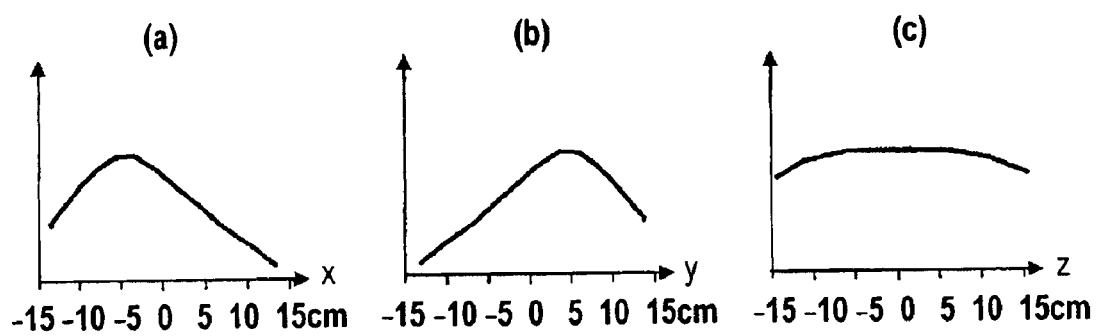
FIGS. 16(a), 16(b) and 16(c) are graphs showing sensitivity distributions of one of the loop coils according to the present invention.

FIG. 16(*a*), FIG. 16(*b*), and FIG. 16(*c*) show respective sensitivity distributions of the loop coil 91-3 along the x-, y-, and z-axes passing through the origin.

Here, the imaging condition is set such that the FOV is 250 mm and the slicing width is 5 mm. The imaging section is set to a transverse plane (xz plane). When the phase-encoding direction is the x-axis, the imaging speed-up ratio can be improved by three times, since the sensitivity distributions of the loop coils 91-1 and 91-3 on the x-axis are not uniform. When the phase-encoding direction is the z-axis, the imaging speed-up ratio also can be improved by three times, since the sensitivity distributions of the figure-eight coils 92-1 and 92-2 on the z-axis are not uniform. When the above-described speed-up technique is applied to an echo planer method, which is the fastest imaging sequence at the present times, and the imaging speed-up ratio is set as three times, one image can be obtained within about 0.03 seconds. This imaging speed is sufficient for imaging a tissue that moves fast, such as the heart.

Further, since any of the loop coils 91-1, 91-2, or 91-3 has a sensitivity on any portion of any xz plane, there is no portion in which the sub-coils hardly have a sensitivity, that is, the coils have a sensitivity throughout any arbitrarily chosen cross section.

The following is a description of the case where the imaging section is in the sagittal plane (yz plane). When the phase-encoding direction is the y-axis, the sensitivity distributions of the loop coils 91-1, 91-2, and 91-3 along the y-axis are not uniform. Since the sensitivity distributions of the loop coils 91-1 and 91-3 are substantially equal, only one of the loop coils 91-1 or 91-3 contributes to removal of aliasing artifacts. However, even then, the imaging speed-up ratio can be improved by at least three times.

When the phase-encoding direction is the z-axis, the imaging speed-up ratio can be improved by three times, since the sensitivity distributions of the figure-eight coils 92-1 and 92-2 along the z-axis are not uniform.

Further, since one of the loop coils 91-1, 91-2, or 91-3 has a sensitivity in an arbitrary portion on an arbitrary yz plane, there is no portion in which the sub-coils hardly have a sensitivity; that is, the coils have a sensitivity throughout the area imaged.

The following is a description of the case where the imaging section is on the coronal plane (xy plane). When the phase-encoding direction is the x-axis, the imaging speed-up ratio can be improved by three times, since the sensitivity distributions of the loop coils 91-1 and 91-3 along the x-axis are not uniform.

When the phase-encoding direction is the y-axis, the imaging speed-up ratio also can be improved by three times, since the sensitivity distributions of the loop coils 91-1, 91-2 and 91-3 along the y-axis are not uniform. Since the sensitivity distributions of the loop coils 91-1 and 91-3 are substantially equal along the line of x=0, only one of the loop coils 91-1 and 91-3 contributes to removal of aliasing artifacts. However, even then, at least the imaging speed-up ratio can be improved by three times.

Further, in an arbitrary portion on an arbitrary xy plane, one of the loop coils 91-1, 91-2, or 91-3 has a sensitivity, whereby there is no portion of the imaging section in which the sub-coils hardly have a sensitivity; that is, one sub-coil has a sensitivity throughout the imaging section.

Figure 17:
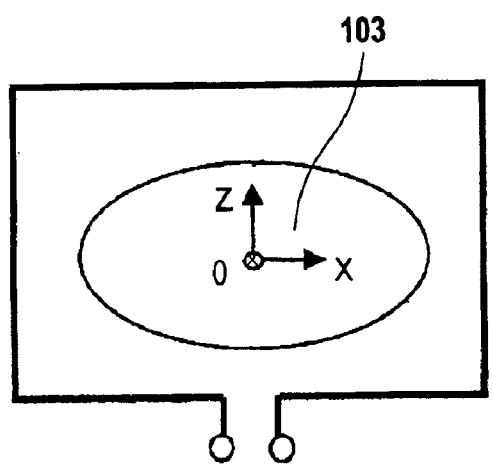
FIG. 17 is a diagram showing an example of the shape of loop coil according to the present invention.

Although an elliptic loop coil is shown in FIG. 9, a rectangular loop coil as shown in FIG. 17 may also be employed. Also, the shape of a rectangular bend in the vicinity of the ends of opposing sides may be employed.

When the coils are actually arranged, the sub-coils are fixed to and supported by a bobbin made by such a material as acryl. The shape of the bobbin preferably is a cylinder or an ellipse cylinder, or a pipe having a rectangular cross-section.

Figure 18:
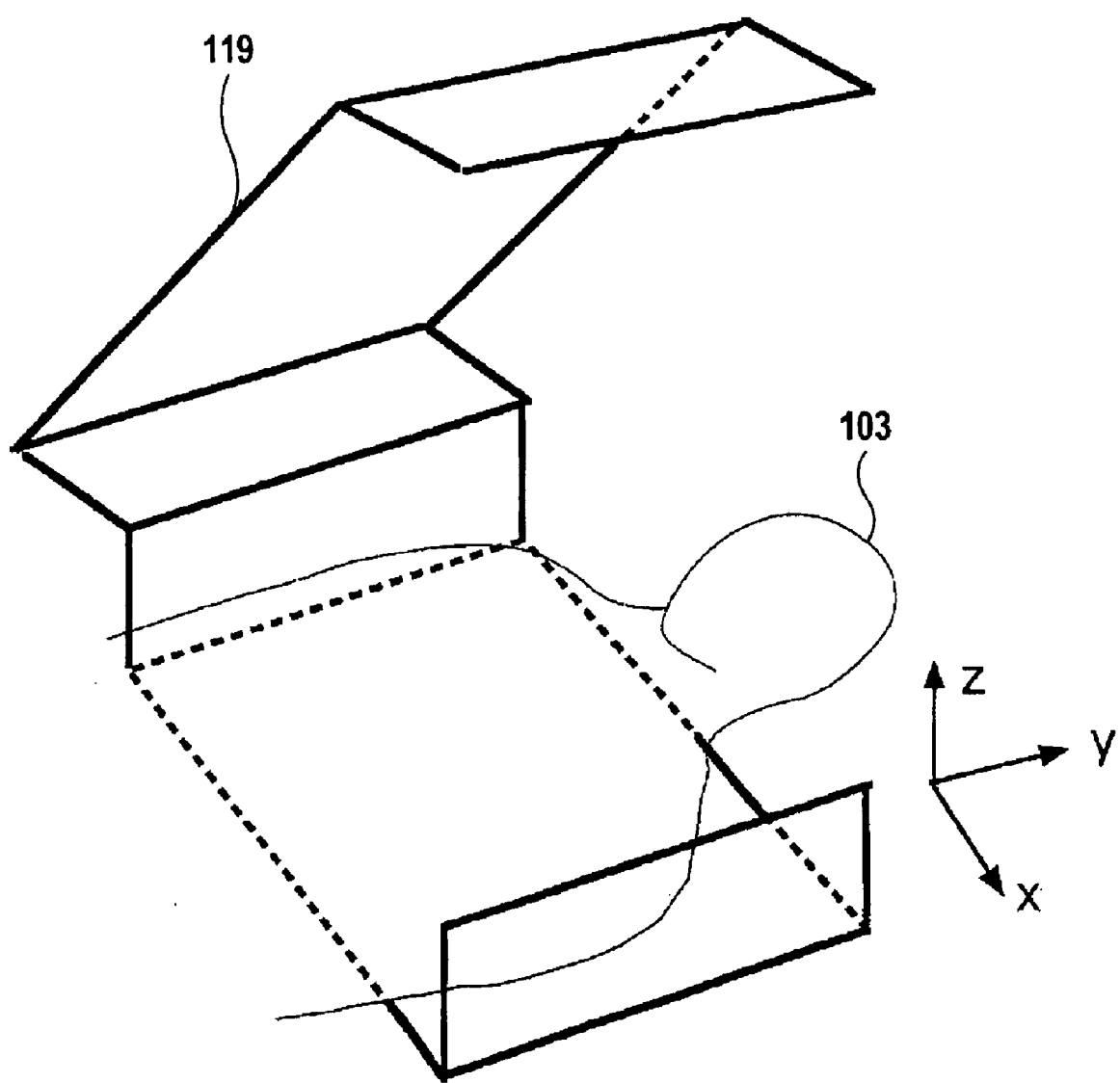
FIG. 18 is a diagrammatic view showing an example of the shape of a bobbin according to the present invention.

As shown in FIG. 18, if the bobbin 119 can be taken apart and put together, it becomes easy to mount the coils on the object. In this case, the coil fixed to the bobbin is also made such that it can be taken off and put on where the bobbin is taken apart. A connector is provided where the coil is taken apart, by which the connector coil is installed.

The following is a description of the case where the phase-encoding direction is the z-axis. Three rectangular FOVs, one-third in the phase encoding direction of a desired FOV, are simultaneously imaged by five coils (⅓ imaging time). Although each of the three one-third FOV images has aliasing artifacts, the artifacts can be removed by solving the simultaneous equations utilizing the difference among sensitivity distributions of the five coils, and a 1/1 FOV image is reconstructed. In this case, there are five simultaneous equations with three unknowns, and there are at least three independent equations on all lines, so that solutions can be obtained.

The description of an embodiment of the present invention has been set forth above. However, the invention is not limited to the above-described embodiment. For example, the number of the sub-coils may be five or more. Further, the number of pixels to be finally obtained may be 64×64, or 128×128, or 256×256.

By employing the reception coil according to the present invention in an open MRI apparatus of the vertical magnetic field type, whichever axis is selected as the phase-encoding direction, the imaging speed-up ratio can be improved by three times, and there is no portion of the imaging section in which the sub-coils hardly have a sensitivity; that is, the sub-coils have a sensitivity throughout the area being imaged.

An open MRI apparatus of the vertical magnetic field type according to the present invention is not limited to selection of an imaging section and a phase-encoding direction, whereby the apparatus fulfills the needs of the user, especially in imaging employed during surgery (IVR) of the heart.

Figure 19:
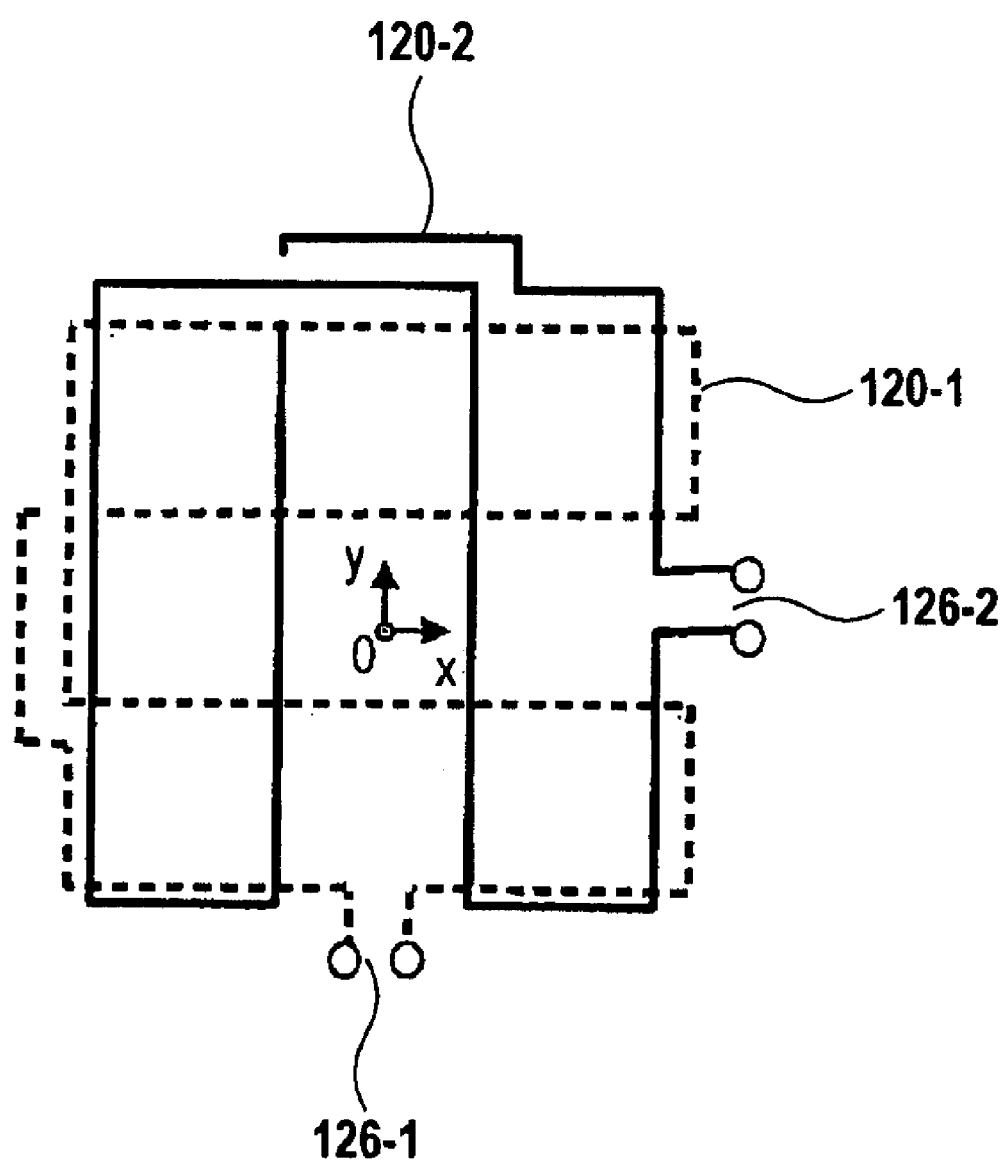
FIG. 19 is a diagram showing an example of an arrangement of the surface coils according to the present invention.

Although the surface coils shown in FIG. 9 are arranged inside the loop coils, they may be arranged outside the loop coils. Although one of the surface coils shown in FIG. 9 is arranged in the vicinity of the body surface on the back side and the other is arranged in the vicinity of the body surface on the chest side, both of them may be arranged in the vicinity of body surface on the chest side or both of them may be located on the back side. When both surface coils are arranged in the vicinity of the body surface on the chest side or both on the back side, the surface coils 120-1 and 120-2 may be arranged such that one of these coils is arranged perpendicular to the other and is overlapped on the other, as shown in FIG. 19. In this case, the output terminals 126-1 of the surface coil 120-1 and the output terminals 126-2 of the surface coil 120-2 are located perpendicular to each other. As shown in FIG. 7(a), the figure-eight coils shown in FIG. 19 have two rectangular conductive loops which are separated from each other.

Figure 20:
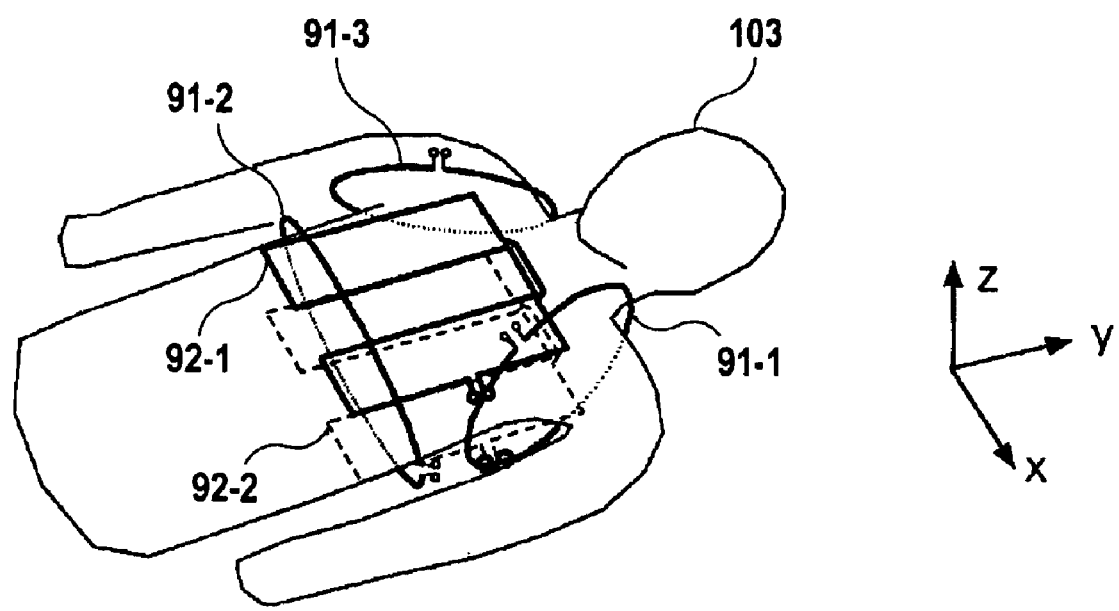
FIG. 20 is a diagrammatic view showing an example of an arrangement of a reception coil according to the present invention.

Although the loop coil 91-1 and the loop coil 91-3 intersect with each other in FIG. 9, they may be arranged such that they do not intersect with each other, as shown in FIG. 20. In FIG. 20, the loop coil 91-1 and the loop coil 91-3 are arranged on the peripheries of the object 103, from the shoulder to the armpit.

When the coil arrangement shown in FIG. 20 is employed, the point where the sensitivity of the loop coil 91-1 is maximized shifts in the plus direction of the x-axis, and the point where the sensitivity of the loop coil 91-3 is maximized shifts in the minus direction of the x-axis, in comparison with the case where the coil arrangement shown in FIG. 9 is employed. Consequently, when the coil arrangement shown in FIG. 20 is employed to carry out the above-described speed-up technique according to the present invention, the S/N ratio in images of the right and left lungs is raised in comparison with the case where the coil arrangement shown in FIG. 9 is employed. Although the loop coil 91-2 is arranged on the periphery of the chest in FIG. 9 and FIG. 20, it may be arranged on the periphery of the neck of the object 103. When the loop coil 91-2 is arranged on the periphery of the neck and the speed-up technique according to the present invention is applied, the S/N ratio in images of portions above the heart is raised. That is, it is advantageous to employ the above speed-up technique in the diagnosis of blood vessels above the heart.

The effect of the present invention has been described for the case where the basic three planes, i.e., the transverse plane (xz plane), coronal plane (xy plane), and sagittal plane (yz plane), are selected as the imaging sections. However, not only these basic planes, but also oblique sections, can be imaged, since the directions of the gradient magnetic fields can be freely determined. The oblique slice imaging is advantageous when an organ whose axis is oblique to the body axis, such as the heart, is imaged.

Figure 21:
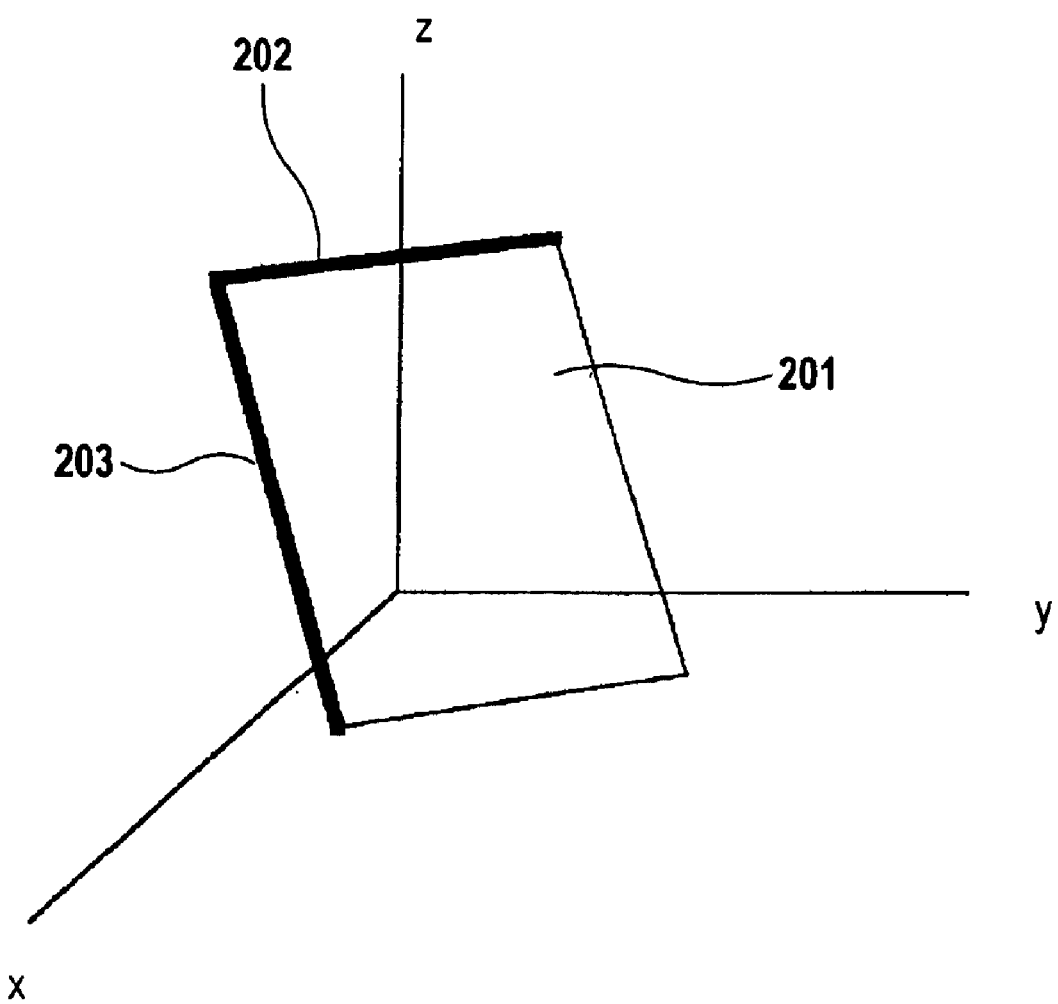
FIG. 21 is a diagram showing an imaging section of an arbitrary orientation according to the present invention.

Such a section 201, in an arbitrary orientation as shown in FIG. 21, can be easily imaged by transmitting current to gradient magnetic field coils in the x-, y-, and z-directions corresponding to the components of magnetic field gradient in the respective directions. In FIG. 21, two axes 202 and 203, that are perpendicular to each other, determine the imaging section 201, and either direction of the axis 202 or 203 is set as the phase-encoding direction. Also, in the oblique imaging shown in FIG. 21, the reception coil has a plurality of loop coils, which are arranged on the periphery of the object within a plane including a line segment parallel to the static magnetic field direction, and a plurality of surface coils, which are arranged on the surface of the object, within a plane including a line segment perpendicular to the static magnetic field direction, whereby the imaging speed-up ratio can be improved by three times, whichever axis is selected as the phase-encoding direction; and, there is no portion of the imaging section in which the sub-coils hardly have a sensitivity when the above-described speed-up technique is applied using the reception coil for an open MRI apparatus of the vertical magnetic field type.

In the MRI apparatus of the vertical magnetic field type according to the present invention, a reception coil has a plurality of loop coils arranged on the periphery of the object within a plane including a line segment parallel to the static magnetic field direction and a plurality of surface coils arranged in the vicinity of the surface of the object within a plane including a line segment perpendicular to the static magnetic field direction, whereby, whichever axis is set as the phase-encoding direction, an arbitrary FOV (1/1 FOV image) can be obtained, while the imaging speed-up ratio can be improved by three times or more in comparison with imaging with the usual method using one coil; and, there is no portion of the cross section in which the sub-coils hardly have a sensitivity; that is, the sub-coils have a sensitivity in all areas in the imaging section.

What is claimed is:

1. An MRI apparatus comprising:
   means for generating a static magnetic field in a vertical direction;
   means for generating an exciting RF pulse to be applied to an object to be examined that is placed in the static magnetic field;
   means for generating gradient magnetic fields to be applied to the object that is placed in the static magnetic field; and
   a reception coil having a plurality of sub-coils for detecting nuclear magnetic resonance signals generated from the object,
   wherein said sub-coils include a plurality of surface coils arranged in the vicinity of the surface of the object within a plane perpendicular to the static magnetic field direction and a plurality of loop coils arranged on the periphery of the object within a plane including an axis parallel to the static magnetic field direction,
   two or more of said sub-coils have nonuniform sensitivity distributions along either of two axes determining an arbitrary imaging section in the object, and
   at least one of said sub-coils has a sensitivity at an arbitrary position in the arbitrary imaging section.

2. An MRI apparatus according to claim 1, wherein the number of said loop coils is three or more, and the number of said surface coils is two or more.

3. An MRI apparatus according to claim 1, wherein said surface coils are arranged inside the plurality of said loop coils.

4. An MRI apparatus according to claim 1, wherein said surface coils are arranged outside the plurality of said loop coils.

5. An MRI apparatus according to claim 1, wherein the surface coils are figure-eight surface coils.

6. An MRI apparatus according to claim 1, wherein said two or more surface coils include a first figure-eight surface coil and a second figure-eight surface coil overlapping with the first figure-eight surface coil, and the location of output terminals of the first figure-eight surface coil is perpendicular to the location of output terminals of the second figure-eight surface coil.

7. An MRI apparatus according to claim 1, wherein the shape of said loop coil is a rectangular shape or a rectangle bend in the vicinity of the ends of opposing sides.

8. An MRI apparatus according to claim 1, wherein, rectangular FOVs having 1/N (N is an integer, no less than two) length of the imaging section in the phase-encoding direction is set in the imaging, aliasing artifacts are removed from an image of the object obtained in the imaging based on the difference between sensitivity distributions of the plurality of sub-coils, and the image of the imaging section is reconstructed.

9. An MRI apparatus according to claim 8, wherein the phase-encoding direction is one of the x-, y-, and z-directions when a rectangular coordinate system is set as (x, y, z) and the vertical direction is set to the z-direction.

10. An MRI apparatus according to claim 1, wherein said plurality of surface coils sandwich the object therebetween, and said two or more of said sub-coils have nonuniform sensitivity distributions along both of the two axes determining the arbitrary imaging section in the object.

11. An MRI apparatus according to claim 1, wherein the plurality of loop coils surround the object and are arranged within respective non-parallel planes, each of the nonparallel planes including an axis parallel to the static magnetic field direction.

12. An MRI apparatus, being definable in a rectangular coordinate system (x, y, z) in which the z axis is in the vertical direction, and the y axis is along the body axis of an object, comprising:
means for generating a static magnetic field in the z-direction;
means for generating an exciting RF pulse to be applied to the object placed in the static magnetic field;
means for generating gradient magnetic fields in the x-direction, the y-direction, and the z-direction; and
a reception coil having five or more sub-coils for detecting nuclear magnetic resonance signals that are generated from the object,
wherein said sub-coils include a first figure-eight surface coil arranged in the vicinity of the surface of the object within a fourth plane parallel to the xy plane, a second figure-eight surface coil overlapping said first figure-eight surface coil arranged within the fourth plane, a first loop coil arranged on the periphery of the object within a first plane parallel to the xy plane, a second loop coil arranged on the periphery of the object within a second plane intersecting with the first plane at about a 45° angle, and a third loop coil arranged on the periphery of the object within a third plane intersecting with the first plane at about a −45° angle.

13. An MRI apparatus according to claim 12, wherein said first and second surface coils are arranged inside said first, second, and third loop coils.

14. An MRI apparatus according to claim 12, wherein said first and second surface coils are arranged outside said first, second, and third loop coils.

15. An MRI apparatus according to claim 12, wherein an arbitrary imaging section in the object is determined by two axes that are perpendicular to each other.

16. An MRI apparatus comprising:
means for generating a static magnetic field in a vertical direction;
means for generating an exciting RF pulse to be applied to an object that is placed in the static magnetic field;
means for generating gradient magnetic fields to be applied to the object that is placed in the static magnetic field; and
a reception coil having five or more sub-coils for detecting nuclear magnetic resonance signals that are generated from the object,
wherein said sub-coils include two or more surface coils arranged in the vicinity of the surface of the object within a plane perpendicular to the vertical direction and three or more loop coils arranged on the periphery of the object and said two or more surface coils within a plane including an axis parallel to the vertical direction,
said two or more sub-coils have nonuniform sensitivity distributions along either of two axes perpendicular to each other, which determine an arbitrary imaging section of the object, and
at least one of said sub-coils has a sensitivity at an arbitrary position in the arbitrary imaging section.

17. An MRI apparatus according to claim 16, wherein said plurality of surface coils sandwich the object therebetween, and said two or more of said sub-coils have nonuniform sensitivity distributions along both of the two axes determining the arbitrary imaging section in the object.

18. An MRI apparatus according to claim 16, wherein the plurality of loop coils surround the object and are arranged within respective non-parallel planes, each of the nonparallel planes including an axis parallel to the static magnetic field direction.

19. An MRI apparatus comprising:
means for generating a static magnetic field in a vertical direction;
means for generating an exciting RF pulse to be applied to the object that is placed in the static magnetic field;
means for generating gradient magnetic fields to be applied to the object that is placed in the static magnetic field; and
a reception coil having five or more sub-coils for detecting nuclear magnetic resonance signals that are generated from the object,
wherein said sub-coils include two or more surface coils arranged in the vicinity of the surface of the object within a plane perpendicular to the vertical direction, and three or more loop coils arranged on the periphery of the object within a plane including an axis parallel to the vertical direction.

20. An MRI apparatus according to claim 19, wherein said two or more sub-coils have nonuniform sensitivity distributions along either of two axes perpendicular to each other, which determine an arbitrary imaging section in the object to be imaged, at least one of said sub-coils has a sensitivity at an arbitrary position in any arbitrary imaging section, and at least two of the nonuniform sensitivity distributions of said sub-coils are different from each other along a line parallel to either of said two axes.

21. An MRI apparatus according to claim 20, wherein said plurality of surface coils sandwich the object therebetween, and said two or more of said sub-coils have nonuniform sensitivity distributions along both of the two axes determining the arbitrary imaging section in the object.

22. An MRI apparatus according to claim 19, wherein said surface coils are arranged inside said three or more loop coils.

23. An MRI apparatus according to claim 19, wherein said surface coils are arranged outside said three or more loop coils.

24. An MRI apparatus according to claim 19, wherein the plurality of loop coils surround the object and are arranged within respective non-parallel planes, each of the nonparallel planes including an axis parallel to the static magnetic field direction.

25. An MRI apparatus utilizing nuclear magnetic resonance, in which gradient magnetic fields and an exciting RF pulse are applied to an object that is placed in a static magnetic field, nuclear magnetic resonance signals generated from the object are detected by a reception coil having plurality of sub-coils, and a sectional image of the object is obtained, wherein said reception coil includes a plurality of first sub-coils arranged in the vicinity of the surface of the object within a plane perpendicular to the static magnetic field direction, and a plurality of second sub-coils arranged on the periphery of the object within a plane including an axis parallel to the static magnetic field direction.

26. An MRI apparatus according to claim 25, wherein said reception coil includes two or more first sub-coils and three or more second sub-coils.

27. An MRI apparatus according to claim 25, wherein the plurality of said second sub-coils surround the object and are arranged within respective nonparallel planes, each of the non-parallel planes including an axis parallel to the static magnetic field direction.

28. An MRI apparatus according to claim 25, wherein two or more of at least one of said plurality of said first sub-coils sandwich the object therebetween and said plurality of second sub-coils surround the object and have non-uniformity sensitivity distributions along at least two axes perpendicular to each other, which determine an arbitrary imaging section of the object.

29. An MRI apparatus comprising:
   means for generating a static magnetic field in a vertical direction;
   means for generating an exciting RF pulse to be applied to an object to be examined that is placed in the static magnetic field;
   means for generating gradient magnetic fields to be applied to the object that is placed in the static magnetic field; and
   a reception coil having a plurality of sub-coils for detecting nuclear magnetic resonance signals generated from the object,
   wherein said sub-coils include a plurality of surface coils arranged within a plane perpendicular to the static magnetic field direction and a plurality of loop coils arranged so as to surround the object within a plane including an axis parallel to the static magnetic field direction.

30. AN MRI apparatus according to claim 29, wherein the plurality of surface coils sandwich the object therebetween, and at least one of the plurality of loop coils surrounds the object and at least a pair of the plurality of surface coils which sandwich the object therebetween.

31. AN MRI apparatus according to claim 29, wherein at least one of the plurality of loop coils extends in a direction substantially perpendicular to an axis of the object.

32. AN MRI apparatus according to claim 29, wherein the plurality of loop coils includes at least three loop coils.

* * * * *